United States Patent [19]

Sharma

[11] Patent Number: 4,594,319

[45] Date of Patent: Jun. 10, 1986

[54] PROTEIN KINASE ENZYME AUT-PK 500 AND A RADIOIMMUNOASSAY FOR DETECTION OF NEOPLASIA

[75] Inventor: Rameshwar K. Sharma, Memphis, Tenn.

[73] Assignee: The University of Tennessee Research Corp., Knoxville, Tenn.

[21] Appl. No.: 590,712

[22] Filed: Mar. 19, 1984

[51] Int. Cl.$^4$ .................... C12Q 1/00; G01N 33/54; C12N 9/12; C07G 7/00

[52] U.S. Cl. ........................................ 435/7; 435/15; 435/29; 435/194; 435/810; 436/519; 436/536; 436/543; 436/544; 436/545; 436/546; 436/804; 436/809; 436/813; 436/815; 424/1.1; 530/387; 530/806

[58] Field of Search .................... 260/112 R; 436/514–516, 518, 536–542, 543–547, 519, 804, 808–811, 813, 815; 435/4, 7, 15, 194, 810, 188, 29; 424/1.1, 9, 85, 88, 93, 177; 206/569

[56] References Cited

U.S. PATENT DOCUMENTS

| | | |
|---|---|---|
| 3,853,987 | 12/1974 | Dreyer ................................. 424/1 |
| 3,985,867 | 10/1976 | Redshaw ............................ 424/1.5 |
| 4,278,653 | 7/1981 | Harris et al. ........................ 424/1 |

OTHER PUBLICATIONS

Klein, J., Immunology, *The Science of Self-Nonself Discrimination*, J. Wiley & Sons, N.Y. (1982), pp. 394–407.
Rose, N. R. et al, *Methods in Immunodiagnosis*, vol. 2nd, ed., J. Wiley & Sons (1980), pp. 147–202.
Ganguly, C. L., Dissert. Abstracts Int. B., #DA8326710, vol. 44(8), 2402 (1983).
Fleischer, N. et al, Methods in Enzymology, vol. 74, pp. 310–320 (1981).
Shanker, G. et al, J. Biol. Chem., vol. 255(8), pp. 3503–3507 (1980).
Shanker, G. et al, Proc. Natl. Acad. Sci., USA, vol. 76(1), pp. 66–70 (1979).
Ganguly, C. et al, J. Biol. Chem., vol. 259(9), pp. 5959–5969 (1984).
Kuroda, Y. et al, Bioch. Biophys. Res. Commun., vol. 112(3), pp. 884–890 (1983).
Sharma, R. et al, Cell. Mol. Biol., vol. 26(1), pp. 65–73 (1980).
Moore, R. E. et al, Cell. Mol. Biol., vol. 25(6), pp. 435–443 (1979).
Yalow and Berson, "General Principles of Radioimmunoassay," Veterans Administration Hosp., Bronx, NY, pp. 7–41.
Green and Gruverman, "Radioactive Drugs", vol. 19, pp. 631–632.

*Primary Examiner*—Thomas G. Wiseman
*Assistant Examiner*—M. Moskowitz
*Attorney, Agent, or Firm*—George W. Neuner; Ernest V. Linek

[57] ABSTRACT

This invention is directed to AUT-PK 500, a novel autophosphorylating protein kinase, to the purification and characterization of AUT-PK 500 from rat adrenocortical carcinoma, to the use of AUT-PK 500 as a marker for neoplasia cells, and to a radioimmunoassay for detecting AUT-PK 500 in neoplasia cells.

22 Claims, 16 Drawing Figures

PROTEIN KINASE ENZYME AUT-PK 500 AND A RADIOIMMUNOASSAY FOR DETECTION OF NEOPLASIA

The United States Government has rights in this invention pursuant to Grant No. CA-16091 awarded by the National Cancer Institute.

FIELD OF THE INVENTION

The present invention is directed to a novel autophosphorylating enzyme, AUT-PK 500, which serves as a marker to aid in the diagnosis and to monitor the progress of neoplasia, to antibodies raised against this enzyme, and to a radioimmunoassay useful for diagnosing neoplasia.

BACKGROUND OF THE INVENTION

Modification of a polypeptide by the process of phosphorylation is an important cellular control mechanism (Greengard, P., *Science*, 199, 146-152 (1978)) and Krebs, E. G. and Beavo, J. A., *Ann. Rev. Biochem.*, 48, 923-959 (1979)). The protein kinases which modulate the activity of phosphopeptides act as mediators for effector molecules such as cyclic nucleotides or non-cyclic nucleotides, and are termed cyclic nucleotide-dependent or cyclic nucleotide-independent protein kinases. While a great deal is known about the structure, mechanism of activation, and in certain cases the biological function of cyclic AMP- and cyclic GMP-dependent protein kinases (Sharma, R. K., *Progress in Nucleic Acid Research and Molecular Biology*, (Cohn, W. E., ed.) Vol. 27, pp. 233-288, Academic Press, New York (1982)), it is only recently that the importance of cyclic nucleotide-independent protein kinases in cellular regulation has begun to be appreciated. A variety of enzymes such as phosphorylase kinase (Cohen, P., Burchell, A., Foulkes, J. G., Cohen, P. T. W., Vanaman, T. C., and Nairn, A. C., *FEBS Lett.*, 92, 287-293 (1978) and Depaoli-Roach, A. S., Roach, P. J., and Larner, J., *J. Biol. Chem.*, 254, 4212-4219 (1979)), myosin light chain kinase (Dabrowska, R., Sherry, J. M. F., Aromatorio, D. K., and Hartshorne, D. J., *Biochemistry*, 17, 253-258 (1978); Yagi, K., Yazawa, M., Kakiuchi, S., Ohshima, M., and Uenishi, K., *J. Biol. Chem.*, 253, 1338-1340 (1978); Hathaway, D. R., and Adelstein, R. S., *Proc. Natl. Acad. Sci. U.S.A.*, 76, 1652-1657 (1979); Walsh, M. P., Vallet, B., Autric, F., and Demaille, J. D., *J. Biol. Chem.*, 254, 12,136-12,144 (1979); and Adelstein, R. S., and Klee, C. B., *J. Biol. Chem.*, 256, 7501-7509 (1981)) and glycogen synthase kinase (Payne, M. E., and Soderling, T. R., *J. Biol. Chem.*, 255, 8054-8056 (1980)) are now known to be regulated by calcium-calmodulin, and therefore are termed calcium-calmodulin-dependent protein kinases. A new species of protein kinase, termed C-kinase, which is calmodulin-independent, but calcium-phospholipid-dependent, has also been reported (Takai, Y., Kishimoto, A., Iwasa, Y., Kawahara, Y., Mori, T., and Nishizuka, Y., *J. Biol. Chem.*, 254, 2692-3695 (1979) and Wise, B. C., Raynor, R. L., and Kuo, J. F., *J. Biol. Chem.*, 257, 8481-8488 (1982)). In addition to these protein kinases which regulate the activity of three recognized general mediators of hormone action, cyclic AMP, cyclic GMP, and calcium, other protein kinases specifically regulating the activity of more specialized molecules such as hemin, double-stranded RNA and epidermal growth factor have also been characterized and are named as hemin-controlled repressor (Farrell, P. J., Balkow, K., Hunt, T., Jackson, R. J., and Traschel, H., *Cell*, 11, 187-200 (1977); Gross, M., Rabinovitz, M., *Biochem. Biophys. Res. Commun.*, 50, 832-838 (1973); Ranu, R. S., and London, I. M., *Proc. Natl. Acad. Sci. U.S.A.*, 73, 4349-4353 (1976); Trachsel, H., Ranu, R. S., and London, I. M., *Proc. Natl. Acad. Sci. U.S.A.*, 75, 3654-3658 (1978); and Tahara, S. M., Traugh, J. A., Sharp, S. B., Lundak, T. S., Safer, B., and Merrick, W. C., *Proc. Natl. Acad. Sci. U.S.A.*, 75, 789-793 (1978)), dsRNA-activated inhibitor (Farrel et al., supra; Levin, D. H., and London, J. M., *Proc. Natl. Acad. Sci. U.S.A.*, 75, 1121-1125 (1978), and Lenz, J. R., and Baglioni, C., *J. Biol. Chem.*, 253, 4219-4233 (1978)), and epidermal growth factor receptor protein kinase (Ushiro, H., and Cohen, S., *J. Biol. Chem.*, 255, 8363-8365 (1980) and Carpenter, G., King., L., and Cohen, S., *J. Biol. Chem.*, 254, 4884-4891 (1979)), respectively. Other tyrosine protein kinases, that apparently regulate the activity of various RNA tumor viruses, also have been characterized (Witte, O. N., Dasgupta, A., and Baltimore, D., *Nature* (London), 283, 826-831 (1980); Eckhart, W., Hutchinson, M. A., and Hunter, T., *Cell*, 18, 925-933 (1979); and Beemon, K., *Cell*, 24, 145-153 (1981)). Further, there are additional protein kinases such as casein kinases I and II, (Hathaway, G. M., and Traugh, J. A., *J. Biol. Chem.*, 254, 762-768 (1979); and Tuazon, P. T., Bingham, E. W., and Traugh, J. A., *Eur. J. Biochem.*, 94, 497-504 (1979)) and protease activated kinases I, (Tahara, S. M., and Traugh, J. A., *J. Biol. Chem.*, 256, 11,558-11,564, (1981)) and II (Tuazon, P. T., Merrick, W. C., and Traugh, J. A., *J. Biol. Chem.*, 255, 10,954-10,958 (1980)), whose primary regulators and biological functions are unknown. Similarly, neither the primary regulator of self-phosphorylating histidine protein kinase, SPK 380, nor its biological functions is known (Kuroda, Y., and Sharma, R. K., *Arch. Biochem. Biophys.*, 217, 588-596 (1982)) although the partially purified enzyme phosphorylates the alpha subunit of the eukaryotic initiation factor 2 in vitro (Kuroda, Y., Merrick, W. C., and Sharma, R. K., *Arch. Biochem. Biophys.*, 213, 271-275 (1982)).

SUMMARY OF THE INVENTION

This invention is directed to AUT-PK 500, a novel autophosphorylating protein kinase, to the purification and characterization of AUT-PK 500 from rat adrenocortical carcinoma, to the use of AUT-PK 500 as a marker for neoplasia cells, and to a radioimmunoassay for detecting AUT-PK 500 in neoplasia cells.

The autophosphorylating enzyme of this invention is characterized by (a) molecular weight as determined by sucrose density sedimentation—490,000; (b) molecular weight as determined by ultracentrifuge—481,400 ($\pm 7\%$); (c) asymmetric molecular configuration; (d) frictional coefficient—1.28; (e) sedimentation coefficient—18.20; (f) Stokes radius—66 angstroms; (g) optimum activity pH—7.5; (h) pI—4.6; (i) phosphate bond—acid stable and alkali labile; (j) autophosphorylates serine residues not threonine; (k) activity unaffected by polyarginine; (l) autophosphorylation activated by the divalent cations $Mg^{2+}$, $Mn^{2+}$, $Sr^{2+}$, $Co^{2+}$ or $Ca^{2+}$.

It has been discovered that the enzyme, AUT-PK 500, is present in neoplasic cells in an amount as much as 250 times that found in normal cells. Thus, the enzyme AUT-PK is a marker for neoplasic cells. The present invention also provides a radioimmunoassay for such neoplasic cells. Antibodies are raised against purified AUT-PK 500. The antibodies are purified and, in one embodiment, the radiolabelled AUT-PK 500 reacts with anti-AUT-PK 500 in the presence of analyte from neoplasic cells to identify such cells by their above normal quantities of AUT-PK 500.

DETAILED DESCRIPTION OF THE INVENTION

In accord with the present invention, a novel autophosphorylating protein kinase, AUT-PK 500, is described. In one embodiment, this novel protein kinase is purified from rat adrenocortical carcinoma. This enzyme is particularly useful as a "marker" for detecting neoplasia. A diagnostic radioimmunoassay kit especially suited for detecting the enzyme in neoplasic cells is also provided by this invention.

Preparations of AUT-PK 500 in accord with this invention have been tested for purity, homogeneity and autophosphorylation with the following results; (a) both one- and two-dimensional polyacrylamide gel electrophoresis of as much as 40 micrograms of the enzyme under denaturing conditions reveal a single stained-band; (b) analyses by immunoelectrophoresis and crossed immune electrophoresis with an immunoglobulin produced against the enzyme demonstrate a single precipitating band; (c) when the enzyme is either phosphorylated with [gamma-$^{32}$P] ATP or iodinated and then immunoprecipitated with specific anti-AUT-PK 500 IgG, resolution of the protein by SDS-polyacrylamide gel electrophoresis followed by radioautographic analysis reveals a single 250,000-dalton phosphorylated or iodinated polypeptide that coincides with the Coomassie Blue-stained band. The purified AUT-PK 500 enzyme preparations in accord with this invention preferably have a specific activity of at least 1000 units/mg and more preferably at least 1500 units/mg.

AUT-PK 500 is unique with respect to the previously described cyclic nucleotide-dependent or -independent protein kinases, because it is not regulated by cyclic nucleotides, by calcium or by calcium-calmodulin. It is also distinct from cyclic nucleotide-independent protein kinases such as casein kinases I and II (Hathaway et al., supra and Tuazon et al., Eur. J. Biochem. supra), the hemin controlled repressor (Farrel et al., supra; Gross et al., supra, Ranu et al., supra and Tahara et al, Proc. Natl. Acad. Sci. U.S.A., supra), the double stranded RNA-activated inhibitor (Farrell et al, supra, Leven et al., supra, and Lenz et al., supra), and protease-activated kinases I and II (Tahara et al, J. Biol. Chem., supra, and Tuazon et al., J. Biol. Chem., supra), because it does not catalyze the phosphorylation of substrates such as casein, eukaryotic initiation factor 2 and histones.

AUT-PK 500 catalyzes the phosphorylation of its serine residue(s) specifically using the terminal phosphate of ATP. This reaction is extremely rapid with half of the phosphorylation sites saturated in about five seconds. Although Mn$^{2+}$ and Mg$^{2+}$ are the most potent activators of AUT-PK 500, other divalent cations such as Co$^{2+}$, Ca$^{2+}$, and Sr$^{2+}$ can also be used. Moreover, polyarginine, which catalyzes the autophosphorylation of cyclic AMP-dependent protein kinase type II (Rosen, O. M., and Erlichman, J., J. Biol. Chem., 250, 7788–7794 (1975)), cyclic GMP-dependent protein kinase (Walton, G. M., and Gill, G. N., J. Biol. Chem., 256, 1681–1688 (1981)), and the 120,000-dalton peptide of adrenocortical self-phosphorylating protein kinase (Kuroda, Y., and Sharma, R. K., Arch. Biochem. Biophys., supra), does not affect the self-phosphorylation of AUT-PK 500.

Indirect immunofluorescence observations with anti-AUT-PK 500 IgG revealed an intracytoplasmic localization of the enzyme in both fixed rat adrenocortical carcinoma 494 (RADC$_4$) cell monolayers and in freshly isolated RADC$_4$ tumor cells. AUT-PK 500 was not apparent in either the nuclei or nucleoli of RADC$_4$ cells. Analyses of viable RADC$_4$ cell membranes were negative, indicating that the localization of AUT-PK 500 was principally intracellular.

Since no readily recognized substrates were phosphorylated by AUT-PK 500, a search was made to identify an endogenous substrate. Initial studies suggested that the phosphorylation of certain rat adrenal cytoplasmic proteins was enhanced by AUT-PK 500 catalyzed phosphorylated protein. Therefore, the AUT-PK 500-dependent phosphorylation of the proteins residing in specialized rat cell components was studied. The immunofluorescence results had revealed a cytoplasmic localization of the enzyme, and since the source of AUT-PK 500 was from rat neoplastic adrenal cortex, cytoplasmic fractions of rat tissues were selected for these studies. The normal tissue counterpart, the rat adrenal gland, is severely limited in size. Therefore, the AUT-PK 500-dependent phosphorylation of proteins contained in membrane-bound ribosomes of rat liver was examined and it was discovered that AUT-PK 500 catalyzed the phosphorylation of a 31,000 molecular weight ribosome protein. This phosphorylation was not inhibited by cyclic AMP-dependent protein kinase inhibitor. The anti-AUT-PK 500 IgG inhibited the AUT-PK 500-dependent phosphorylation of this protein, while the pre-immune rabbit serum IgG was unable to do so. AUT-PK 500-independent phosphorylation of other membrane-bound ribosomal proteins was not influenced by either the specific immune IgG or the pre-immune IgG. These results revealed that the membrane-bound ribosomal protein of 31,000 molecular weight was one specific substrate of AUT-PK 500.

These results indicate that AUT-PK 500 is a novel cyclic nucleotide-independent autophosphorylating protein kinase. The enzyme appears to uniquely regulate the activity of at least one membrane-bound ribosomal protein.

It has further been discovered that AUT-PK 500 exists in excess of 200-fold elevation in adrenocortical carcinoma as compared to normal adrenal gland. Studies on four rapidly growing heptomas, including cultured heptoma cell lines, the pituitary tumor and human mammary carcinoma, indicate that the elevated levels of this protein kinase serves as a general marker of neoplasia, since all malignant cells analyzed contained at least this 200-fold excess of the enzyme in comparison with their normal counterparts. Especially important is the finding that the species barrier in human mammary carcinoma was overcome based on the expression of this enzyme from rat to human malignancy.

By employing standard radioimmunoassay (RIA) techniques, the enzyme level in cell samples has been quantitatively determined. The enzyme is undetectable in normal cells, and its quantitation by RIA has proven useful as an indication of early stage neoplasia. Thus, the enzyme, AUT-PK 500, serves as a tumor marker which may be relied upon for the detection of, and to follow the progress of tumor growth.

Antibodies against AUT-PK 500 may be prepared in accordance with known methods for immunizing test animals, for example, by continuous sub-cutaneous or intramuscular injections of small quantities of AUT-PK 500 in mixture with a suitable adjuvant. The antibodies formed in the animal may then be recovered from the blood serum of the animal by well known techniques. As used herein, the term "antibodies corresponding to anti-AUT-PK 500" refers to antibodies, from whatever source, which behave in a manner analogous to those anti-AUT-PK 500 IgG antibodies obtained from rabbits by continuous subcutaneous and intramuscular injections of AUT-PK 500 at a concentration of 150 micrograms/ml as described infra. Changes in animal, dose regime, and the like may vary either the quantity or type of antibodies raised, but these variations are deemed to be within the scope of the present invention.

Labelling of AUT-PK 500 and/or antibodies against AUT-PK 500 may be effected in a conventional manner, using radiotracers such as Iodine-125, Iodine-131, Cobalt-57 and the like. Other chemical labels, such as fluorescent compounds may also be employed, but radionucleotides are the preferred labels employed herein.

To quantitate the levels of AUT-PK 500 in a test sample of a patient, any of the various RIA techniques known may be employed. RIA techniques are described in; Howantiz, J. H. and Howanitz, P. J., "Radioimmunoassay and Related Techniques", *Clinical Diagnosis and Management*, Henry, J. B., ed., 16th Ed., pp. 385–410, W. B. Saunders Co., Philadelphia, PA, 1979; Yalow, R. S., et al., "General Principles of Radioimmunoassay", *Radioisotopes in Medicine: In Vitro Studies*, Hayes, R. L., et al., Eds., pp. 7–41, U.S. Atomic Energy Commission, Oak Ridge, Tenn., 1968; and U.S. Pat. Nos. 3,853,987; 3,985,867 and 4,278,653.

In general, RIA involves the separation of a radiolabeled antigen, e.g., Iodine-125-AUT-PK 500, into bound and unbound fractions after its interaction with an antibody, e.g., anti-AUT-PK 500 IgG, in the presence of an unknown quantity of unlabeled antigen from a test sample. The ratio of bound-to-free labeled antigen is related to the concentration of unknown antigen in the test sample by comparison to a curve demonstrating binding in the presence of standards of known concentration. (Zettner, A. and Duly, P. E., *Clin. Chem.*, 20, 5 (1974)) For example, a radioimmunoassay can be based on the competitive binding of radiolabeled AUT-PK 500 and unlabeled AUT-PK 500 with the anti-AUT-PK 500 IgG antibody in vitro. By holding the antibody concentration and the radiolabeled antigen concentration constant, the binding of the label of antigen is quantitatively related to the amount of unlabeled antigen added. Thus, varying concentration standards of AUT-PK 500 are employed to prepare a plot of the fraction of bound radiolabeled AUT-PK 500 against the concentration of AUT-PK 500 added. The amount of unlabeled AUT-PK 500 in an unknown sample may then be determined by measuring the fraction of bound radiolabeled AUT-PK 500 in its presence from the standard curve.

In addition to the single antibody assays described above, double antibody assays may also be employed. A double antibody reaction is useful when low or unknown primary antibody levels are encountered. For example, as described infra, a primary antibody such as rabbit anti-AUT-PK 500 IgG is employed to react with AUT-PK 500 from neoplasic cells. Analysis oof this reaction is then accomplished by immunofluorescence by reacting a second antibody such as, fluorescein-conjugated goat anti-rabbit IgG, with the bound complex of primary antibody and AUT-PK 500.

This invention also encompasses a diagnostic kit for testing samples for neoplasia. The kit includes an ampoule or the like containing antibodies against AUT-PK 500, preferably in freeze-dried, i.e., lyophylized form, and also an ampoule containing a labeled form of AUT- PK 500, preferably in freeze-dried, i.e., lyophylized form. The kit optionally contains an ampoule of AUT-PK 500 in a predetermined concentration for use as a control.

The invention will be further illustrated with reference to the following examples, which illustrate the invention, but are not to be construed as a limitation on the true scope of the invention, which is set forth in the appended claims. All percentages reported herein, unless otherwise specified, are percent by weight.

MATERIALS

DEAE-cellulose (diethylaminoethyl-cellulose), cyclic nucleotides, histone (type IIA), casein, phosvitin and protamine were purchased from Sigma; ACA-34 Ultragel and ampholine (pH 3.5-10) from LKB; [gamma-$^{32}$P] ATP (3,000 Ci/mmol) and cyclic [$^3$H] AMP (40 Ci/mmol) from Amersham. Phosphocellulose, all of the reagents for SDS-polyacrylamide gel electrophoresis and immunoelectrophoresis including Bis, i.e., (N,N'-methylene-bis-acrylamide), Tris, i.e., (tris(hydroxymethyl)aminomethane) and TEMED, i.e., (N,N,N',N'-tetramethylethylenediamine) were obtained from Bio-Rad (Rockville Centre, NY). Dulbecco's MEM was from GIBCO (Grand Island, NY), and fluorescein-conjugated goat anti-rabbit IgG was from Cappel Laboratories. All other reagents were analytical grade and were obtained commercially.

Cyclic AMP-Sepharose was synthesized by coupling cyclic AMP with epoxy-activated Sapharose and cyclic AMP-dependent protein kinase inhibitor was prepared according to the method of Walsh et al., (*J. Biol. Chem.*, supra).

PROTEIN KINASE ASSAY

Protein kinase activity was measured by the incorporation of $^{32}$P from [gamma-$^{32}$P] ATP into an appropriate substrate. The 250-microliter reaction mixture contained 20 mM Tris-HCl, pH 7.5, 10 mM Mg$^{2+}$, $2.5 \times 10^{-6}$M [gamma-$^{32}$P] ATP (400-600 cpm/pmol) and an appropriate amount of the enzyme. The reaction was incubated at 37° C. for one minute or as specified under experimental conditions, and was terminated by the addition of 2 ml of ice-cold 10% trichloroacetic acid followed by the addition of 500 micrograms of bovine serum albumin. The precipitate was immediately filtered on a GF/C filter and washed three times with 2 ml of ice-cold 10% trichloroacetic acid. The filter was dried and counted in a cocktail of Omnifluor in toluene.

CYCLIC NUCLEOTIDE BINDING ASSAY

Cyclic nucleotide binding assay was performed as previously described (Ahrens, H., Paul, A. K., Kuroda, Y., and Sharma, R. K., *Arch. Biochem. Biophys.*, 251, 597-609 (1982)). An appropriate aliquot of the enzyme was incubated at 0° C. for 60 min in 50 mM sodium acetate buffer (pH 4.0), 2 mM EDTA (Cohen, et al., supra) and 3 pmol of cyclic [$^3$H] AMP ($1 \times 10^5$ cpm/pmol) in a final volume of 100 microliters. The reaction was initiated by the addition of AUT-PK 500 and was terminated with 2 ml of ice-cold 70% saturated ammonium sulfate solution. The precipitate was collected on GF/C filters, washed three times with 25% saturated ammonium sulfate solution, and the filters were dried and counted for radioactivity in 5 ml of Omnifluor cocktail.

AUTOPHOSPHORYLATION AND PURITY OF THE ENZYME

Autophosphorylation of AUT-PK 500 was evaluated by phosphorylating 40 micrograms of enzyme with [gamma-$^{32}$P] ATP, followed by its examination with two-dimensional gel electrophoresis (O'Farrell, *J. Biol. Chem.*, 250, 4007-4021 (1975)), using a nonequilibrium pH gradient (pH 3.5-10), 0.02% urea, 6% acrylamide, 0.2% Bis, 2% NP-40, 2% Ampholines (pH 3.5-10), 0.02% ammonium persulfate, and 0.007% TEMED. In the second dimension, SDS-polyacrylamide gel (0.1% sodium dodecyl sulfate, 6% acrylamide and 0.3% Bis) electrophoresis was conducted in the presence of 20 mM Tris and 154 mM glycine, pH 8.3 (Laemmli, U. D., *Nature*, (London), 227, 680-684 (1970)). The gel was stained with 0.05% Coomassie Brilliant Blue and destained with 7.5% acetic acid. The stained gel was dried and subjected to autoradiography (Moore, R. E., Ahrens, H., and Sharma, R. K., *Cell. Mol. Biol.*, 25, 435-443 (1980)) with the use of Kodak No-Screen film (NS-2T).

Autophosphorylation of AUT-PK 500 was also analyzed by one-dimensional SDS-polyacrylamide gel electrophoresis. The enzyme was incubated in the presence of [gamma-$^{32}$P] ATP. The reaction was terminated with a buffer (Engbaek, C., Gross, R., and Burgess, R., *Mol. Gen. Genet.*, 143, 291-295 (1976)) containing 10% glycerol, 5.6% 2-mercaptoethanol, 3% SDS and 0.0625M Tris-HCl, pH 6.8, in the presence of 0.04% SDS. The phosphorylated sample was applied to 6% acrylamide containing 0.1% SDS and 0.3% Bis. Electrophoresis was conducted in the presence of Tris-glycine buffer, pH 8.3. The gel was stained with Coomassie Brilliant Blue, destained with 7.5% acetic acid, dried and subjected to autoradiography (Moore et al., supra).

The purity of the enzyme was checked by both two-dimensional gel electrophoresis and one-dimensional SDS-polyacrylamide gel electrophoresis. For two-dimensional gel electrophoresis, up to 40 micrograms of AUT-PK 500 was subjected to isolectric focusing in the first dimension followed by SDS-polyacrylamide gel electrophoresis in the second dimension. The gel was stained in 0.005% Coomassie Brilliant Blue/50% ethyl alcohol/7% acetic acid and destained with 7% acetic acid. For SDS-polyacrylamide gel electrophoresis, disc gels ($0.5 \times 12$ cm) were prepared (Engbaek et al., supra; and Orstein, L., *Ann. N.Y. Acad. Sci.*, 121, 321-349 (1964)) and electrophoresis was conducted in Tris-glycine buffer, pH 8.3. The gels were stained with 0.05% Coomassie Brilliant Blue for 2 hr. and destained in 7.5% acetic acid.

ISOELECTRIC FOCUSING

The isoelectric point of AUT-PK 500 was determined under nondenaturing conditions as previously described (Kuroda et al., *Arch. Biochem. Biophys.*, supra). Five percent polyacrylamide (Orstein et al., supra; and Davis, B. J., *Ann. N.Y. Acad. Sci.*, 121, 404-427 (1964)) in 2% ampholite with a pH range of 3.0 to 10.0 was photopolymerized with riboflavin (Ames, G. F. L. and Nikaido, K., *Biochem.*, 15, 616-623 (1976)) in gel tubes ($0.5 \times 12$ cm). Isoelectric focusing was carried out at 4° C. for 15 hr. at 450 V with 10 mM H$_3$PO$_4$ as the anode electrode solution in the lower reservoir chamber and 20 mM NaOH as the cathode electrode solution in the upper reservoir chamber (O'Farrell, supra). The gels were cut into 1.5 mm slices, extracted with 500 microliter deionized, degassed water, and assayed for pH and protein kinase activity.

DETERMINATION OF MOLECULAR WEIGHT, STOKES RADIUS, AND FRICTIONAL COEFFICIENT

The Stokes radius, frictional ratio and molecular weight of AUT-PK 500 were determined by gel-filtration column chromatography using ACA-34 Ultrogel (Siegel, L. E. and Monty, K. J., *Biochim. Biophys. Acta.,* 112, 346–362 (1966)). The protein standards used for the calibration of the column were thyroglobulin (80 angstroms), phosphorylase A (63 angstroms) and catalase (52 angstroms).

Sucrose density gradient was performed (Martin, R. G. and Ames, B. N., *J. Biol. Chem.,* 236, 1372–1379 (1961)), using thyroglobulin (19.4 S), apoferritin (17.6 S) and catalase (11.2 S) as standards.

PREPARATION OF MEMBRANE-BOUND RIBOSOMES

Male Holtzman rats were fed ad libitum until 5:00 p.m. on the day preceding the isolation of membrane-bound ribosomes. At 5:00 p.m. the food was removed. The following morning (8:00 a.m.) the rats were decaptitated and the livers were rapidly removed and chilled in double-distilled water at 4° C. All subsequent procedures were performed at 4° C.

Membrane-bound ribosomes were prepared from posmitochondrial supernatants (Ikehara, Y., and Pitot, H. C., *J. Cell. Biol.,* 59, 28–44 (1973)). The isolated free and membrane-bound ribosomal solutions (70–250 $A_{250}$ units/ml) were stored for as long as 6 months at $-70°$ C. in the presence of 5 mM 2-mercaptoethanol in 20 mM Tris-HCl (pH 7.4).

PHOSPHORYLATION OF MEMBRANE-BOUND RIBOSOMES BY AUT-PK 500

AUT-PK 500, 2–3 micrograms, was incubated in the presence of 20–30 micrograms of membrane-bound ribosomes and $2.5\times10^{-5}$M [gamma-$^{32}$gP] ATP. The reaction volume (50 microliters) also contained 20 mM Tris-HCl, pH 7.5 and 10 mM $Mg^{2+}$. The reaction was carried out at 37° C. for 15 min. and was terminated by the addition of 17 microliters of 4× sample buffer (Engbaek, et al., supra). The phosphorylated proteins were analyzed by SDS-polyacrylamide gel (0.3% Bis, 6% or 10% acrylamide and 0.1% SDS) electrophoresis (Laemmli et al., supra). Electrophoresis was performed in Tris-glycine buffer, pH 8.3 (20 mM Tris and 153 mM glycine). The gel was stained with Coomassie Brilliant Blue, destained with 7.5% glacial acetic acid and dried. The dried gel was subjected to autoradiography (Moore et al., supra) with the use of Kodak NS-2T film.

The phosphorylation of membrane-bound ribosomal proteins also was performed in the presence of 5 micrograms of cyclic AMP-dependent protein kinase inhibitor (Walsh, D. A., Ashby, C. D., Gonzalez, D., Calkins, D., Fischer, E. H. and Krebs, E. G., *J. Biol. Chem.,* 246, 1977–1985 (1971)) to rule out the AUT-PK 500 -dependent phosphorylation of ribosomal protein by the catalytic subunit of cyclic AMP-dependent protein kinase potentially present as a contaminant in the reaction mixture.

PREPARATION OF RABBIT ANTI-AUT-PK 500 IgG

Rabbits were immunized with purified AUT-PK 500 emulsified in complete Freund's adjuvant (GIBCO) to give a final protein concentration of 150 micrograms/ml. One ml of the emulsion was distributed subcutaneously into five sites in the nuchal region, and 1.0 ml was injected intramuscularly into each hind leg muscle. The intramuscular injections were repeated at weekly intervals for 2 weeks. After 8 weeks, the rabbits were boosted with intramuscular injections consisting of SDS-polyacrylamide gel eletrophoresis slices containing the isolated AUT-PK 500 emulsified in incomplete Freund's adjuvant, and blood samples were collected from the ear veins at 3-week intervals thereafter. The sera were pooled, heat-inactivated (56° C., 30 min.), and stored at $-20°$ C. Booster injections were continued at 8-week intervals. IgG fractions were prepared from serum pools by 3× precipitation with $(NH_4)_2SO_4$ followed by DEAE-cellulose chromatography (Garvey, J. S., Cremer, N. E., and Sussdorf, D. H., in *Methods in Immunology, A Lobaratory Test for Instruction and Research,* Third Edition, pp. 218–219, 328–336, 340–346, 394–397, 522, W. B. Benjamin Inc. (1977)). These IgG fractions from immune and normal serum pools were used for all experiments.

BLOCKAGE OF AUTOPHOSPHORYLATION OF AUT-PK 500 AND OF AUT-PK 500-DEPENDENT PHOSPHORYLATION OF MEMBRANE-BOUND RIBOSOMAL PROTEIN

AUT-PK 500, 2–3 micrograms (10 microliters), was incubated in the presence of 10 microliters of rabbit anti-AUT-PK 500 IgG for 15 min. at 4° C. As a control, 10 microliters of pre-immune rabbit serum IgG were substituted for the specific immune IgG. Membrane-bound ribosomes (20–30 micrograms) were added to these mixtures, and the reactions were initiated by the addition of 30 microliters of a solution containing 20 mM Tris-HCl, pH 7.5, 10 mM $Mg^{2+}$ and $2.5\times10^{-5}$M [gamma-$^{32}$P] ATP. The reactions were incubated at 37° C. for 15 min., then terminated with 4× sample buffer (Engbaek, et al., supra). Aliquots of each reaction mixture were analyzed by one dimensional SDS-polyacrylamide gel electrophoresis and autoradiography as described above.

IMMUNOELECTROPHORESIS

Techniques for immunoelectrophoresis and crossed immune electrophoresis have been described (Garvey et al, supra; and Schmidt-Ullrich, R., Wallach, D. F. H., and Davis, F. D. G., *J. Natl. Cancer Inst.,* 57, 1117–1126 (1976)). All tests were performed in 1.0% agarose and 0.1M barbital buffer, pH 8.6 (Williams, C. A. and Chase, M. W. in *Methods in Immunology,* Vol. III, p. 468, Academic Press, New York (1971)). Immunoelectrophoresis patterns were dried and stained with acid fuchsin. The crossed immune electrophoresis patterns were stained with Coomassie blue.

PREPARATION OF TUMOR CELL CULTURES AND SUSPENSIONS FOR IMMUNOFLUORESCENCE

Studies on the intracellular localization of AUT-PK 500 employed converglass monolayers in logarithmic growth prepared from a cloned, established tumor cell line, rat adrenocortical carcinoma 494, RADC$_4$, (Snell, K. C., and Steward, H. L., *J. Natl. Cancer Inst.*, 22, 1119-1155 (1959)) that had been cultured in excess of 220 serial passages. The coverglass cultures were fixed in acetone at 0° C. for 10 min. and stored at −20° C. Freshly isolated tumor cells also were examined for the distribution of AUT-PK 500. For these observations four-week tumors were removed, trimmed of fibrous membranes, sliced into quarters and washed free of the central necrotic tissue in Dulbecco's MEM containing penicillin (50 units/ml) and streptomycin (50 micrograms/ml). The quarters then were minced and stirred rapidly for 60 min. at room temperature. The tumor cells released by agitation were harvested by centrifugation, and the pelleted cells were resuspended, layered on slides and allowed to air-dry. These preparations were fixed in acetone at 0° C. for 10 min. and stored at −20° C. Assays for viable cell membrane localization of AUT-PK 500 used RADC$_4$ cell suspensions released from monolayer cultures with the use of a rubber policeman.

IMMUNOFLUORESCENCE

Indirect immunofluorescence was used to detect the reaction of the specific rabbit anti-AUT-PK 500 IgG with the tumor cells. Fluorescein-conjugated goat anti-rabbit IgG (H and L chain specific) was used to reveal specific binding. The procedures for cytoplasmic studies, viable membrane assays, and for incubation with immunoglobulin have been described (Roberts, A. N., Smith, K. L., Dowell, B. L. and Hubbard, A. K., *Cancer Res.*, 38, 3033-3043 (1978)). Controls to rule out possible nonspecific globulin binding included: (a) indirect assays with the pre-immune rabbit serum IgG substituted for the test IgG in the primary incubation step, and (b) direct tests with the fluorescein-conjugated goat anti-rabbit IgG.

PROTEIN DETERMINATION

Protein concentrations were determined (Bradford, M. M., *Anal. Biochem.*, 72, 248-254 (1976)) using the Bio-Rad reagent and bovine serum albumin as a standard.

CHARACTERIZATION OF THE PHOSPHORYLATED AMINO ACID

To characterize the amino acid residue modified by autophosphorylation of AUT-PK 500, the enzyme (100 micrograms) was incubated for 30 min. with [gamma-$^{32}$P] ATP under standard conditions. The protein was precipitated with acetone and extensively washed with the same solvent, lyophilized, then hydrolyzed with 0.5 ml of 6M HCl at 110° C. for 3 hr. in a vacuum-sealed tube. The hydrolyzate was lyophilized and dissolved in 30 microliters of deionized water containing 30 micrograms each of authentic samples of phosphotyrosine, phosphoserine or phosphothreonine; the amino acids were resolved by high voltage paper electrophoresis (Whatman 3 mm, 1,200 volts, 2 hr., pH 2.0) using glacial acetic acid-formic acid-water (12:3:85 v/v) as an ionizing buffer. The paper was dried, sprayed with ninhydrin to detect amino acid spots and autoradiographed with Kodak NS-2T film.

EXAMPLE 1

Purification of AUT-PK 500

Unless otherwise indicated, all procedures were carried out at 0°-4° C. using deionized water.

Step 1

Homogenization and Ammonium Sulfate Precipitation

Fresh rat adrenocortical carcinoma 494 (RADC$_4$) (Snell et al., supra) was collected in 0.9% NaCl containing 8 mM benzamidine hydrochloride. The tumor tissue (40 g) was cleaned of necrotic debris and surrounding fibrous tissue, then homogenized with 80 ml of 20 mM Tris-HCl buffer containing 6 mM 2-mercaptoethanol, 2 mM EDTA and 10 mM benzamidine hydrochloride (pH 7.5) (buffer A) for two min. The homogenate was centrifuged at 10,000×g for 60 min. Solid ammonium sulfate was added to the supernatant to 60% saturation. The precipitate was dissolved in 20 mM Tris-HCl containing 6 mM 2-mercaptoethanol, 2 mM EDTA, 10 mM benzamidine hydrochloride and 10% glycerol (buffer A, pH 7.5), and dialyzed overnight against the same buffer.

Step 2

DEAE-Cellulose Chromatography

Figure 1:
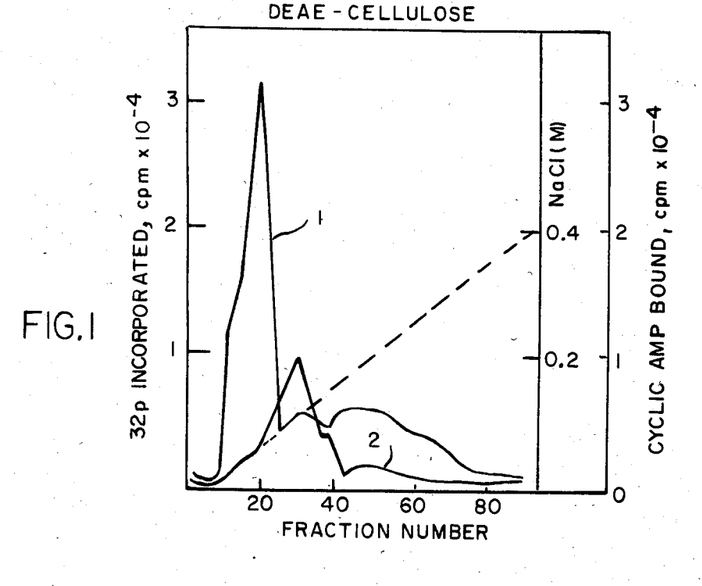
FIG. 1 depicts both protein kinase (1) and cyclic AMP binding (2) results for DEAE-cellulose column chromatography fractions of AUT-PK 500 from rat adrenocortical carcinoma 494.

The dialyzed fraction from Step 1 (1300 mg of protein) was applied to a DEAE-cellulose column (2.8×4 cm) pre-equilibrated with buffer A. The column was washed with 400 ml of buffer A and eluted with 1 liter of a linear 0-400 mM NaCl gradient in buffer A. The peak AUT-PK 500 activity emerged at 60 mM NaCl (FIG. 1) and was distinct from the cyclic AMP-binding peak. The AUT-PK 500 peak fractions were pooled, and ammonium sulfate was added to give a final concentration of 60% saturation. The precipitate was dissolved in 20 mM potassium phosphate buffer, pH 7.0, 6 mM 2-mercaptoethanol, 2 mM EDTA and 8 mM benzamidine hydrochloride (buffer B) and dialyzed overnight against the same buffer.

Step 3

Gel-filtration Chromatography

Figure 2:
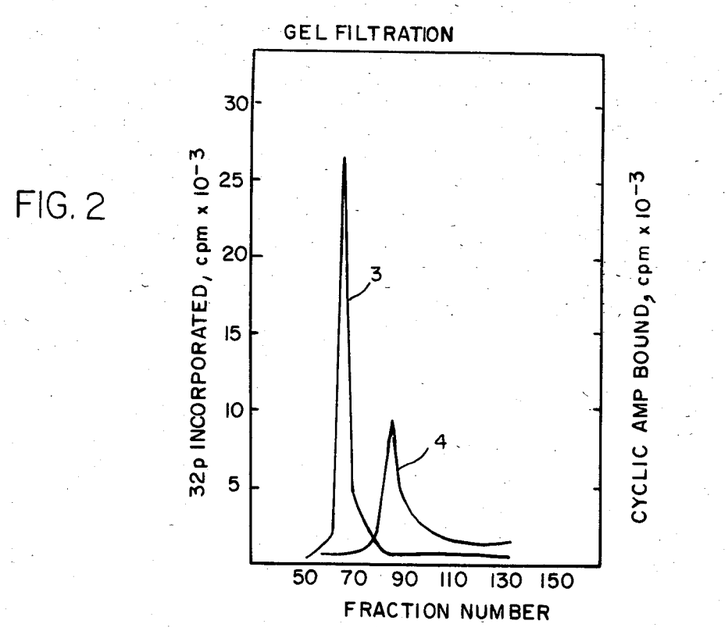
FIG. 2 depicts both protein kinase (3) and cyclic AMP binding (4) results for Ultrogel ACA-34 column chromatography fractions of AUT-PK 500.

The AUT-PK 500 fraction from Step 2 (40 mg) was applied to a 130 ml (1.5×68 cm) ACA-34 column previously equilibrated with buffer B, and eluted with the same buffer. The peak activity fractions were pooled (FIG. 2).

Step 4

Cyclic AMP Affinity Chromatography

In order to ensure the removal of any contaminant cyclic AMP-binding protein, the pooled fractions from Step 3 were equilibrated with 5 ml of cyclic AMP-Sepharose for 1 hr. at 0° C. The resin was transferred to a column and washed with 55 ml of buffer B. The flow-through fraction contained AUT-PK 500.

Step 5

Phosphocellulose Chromatography

The flow-through fraction of AUT-PK 500 from Step 4 was dialyzed against buffer B, and applied to a phosphocellulose column (0.9×2.5 cm) pre-equilibrated with buffer B. The enzyme did not bind to the resin. Flow-through fractions containing enzyme activity were pooled and concentrated by Amicon ultrafiltration.

Eighty percent of the preparations obtained from these purification steps resulted in homogeneous AUT-PK 500 (Table I). In the remaining 20%, the purity was from 85 to 89%, ascertained by densitometer scanning of the enzyme resolved by SDS-polyacrylamide gel electrophoresis. In these instances, additional purification steps were performed, Steps 6 and 7.

TABLE I
Purification of AUT-PK 500 from Rat Adrenocortical Carcinoma

| Fractions | Total Protein (mg) | Specific Activity[B] units/mg | Total Activity[A] (units) | Purification (fold) |
|---|---|---|---|---|
| 1. 60% Ammonium sulfate precipitation of postmitochondrial supernatant | 1300 | 2 | 2660 | 1 |
| 2. DEAE-cellulose | 40 | 56 | 2231 | 28 |
| 3. ACA-gel filtration | 1 | 1350 | 1350 | 675 |
| 4. Cyclic AMP-Sepharose | 0.66 | 1400 | 960 | 700 |
| 5. Phosphocellulose | .33 | 1900 | 633 | 950 |

[A]The amount of enzyme which catalyzed the transfer of one pmol of inorganic phosphate from [gamma-$^{32}$P] ATP into endogenous substrate per minute at 37° C. was taken as one unit.
[B]Specific activity is defined as a Fraction's total activity (in units) divided by that Fraction's protein weight (in mg).

Step 6

Chromatofocusing

If the AUT-PK 500 obtained in Step 5 was insufficiently pure (i.e., <90%), it was further purified by the technique of chromatofocusing (Sluyterman, L.A.A.E., et al., *J. Chromatog.*, 150 17–30 and 31–44 (1978) and *Ion Exchange Chromatography—Principles and Methods,* Pharmacia Fine Chemicals AB, Uppsala, Sweden). The purification directions were strictly followed as described in the instruction manual provided with the Pharmacia Fine Chemicals Chromatofocusing kit. In this technique the protein to be fractionated is absorbed onto an ion exchanger, PBE 94, a pH gradient is developed with appropriate polyamine buffer, and proteins are eluted in the order of their isoelectric points.

AUT-PK 500 was applied to the chromatofocusing gel column (0.9×15 cm) previously equilibrated with 0.25M imidazole-HCl buffer (pH 7.4). The column was eluted with polybuffer 74 (pH 4.0). AUT-PK 500 peak activity appeared at pH 5.0. The peak activity fractions were pooled, precipitated by the addition of solid ammonium sulfate to 60% saturation, dissolved in 20 mM potassium phosphate buffer containing 30 mM 2-mercaptoethanol, 0.2 mM EDTA and 8 mM benzamidine hydrochloride and dialyzed overnight against the same buffer.

Step 7

Gel-filtration Chromatography

AUT-PK 500, from Step 6, was then subjected to the gel-filtration chromatographic step exactly as described in Step 3.

EXAMPLE 2

Purity and Autophosphorylation

Figure 3:
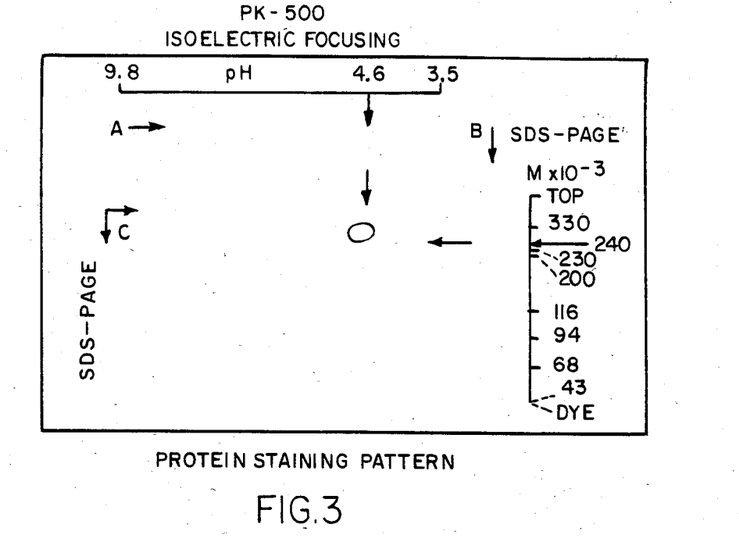
FIG. 3 is the protein staining pattern for one and two dimensional SDS-polyacrylamide gel electrophoresis of AUT-PK 500.
Figure 4:
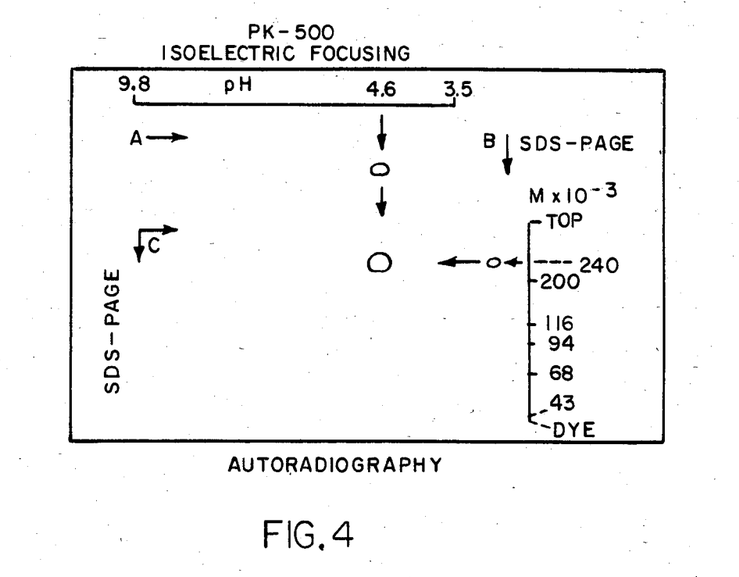
FIG. 4 is the autoradiograph of phosphrylated AUT-PK 500 following one and two dimensional SDS-polyacrylamide gel electrophoresis.

When homogenous AUT-PK 500 was subjected to either one-dimensional or two-dimensional SDS-polyacrylamide gel electrophoresis, a single stained band corresponding to a 250,000 molecular weight was obtained (FIG. 3). The molecular weight of 250,000, based on SDS-polyacrylamide gel, remains unchanged when the enzyme is analyzed under harsh denaturing conditions such as boiling the protein in 6M guanidine hydrochloride and the adding of the reducing agent such as beta-mercaptoethanol. Incubation of the enzyme with [gamma-$^{32}$P] ATP showed an autophosphorylated band that comigrated with the Coomassie Brilliant Blue-stanied band (FIG. 4). These results demonstrated the homogeneity and autophosphorylating property of the enzyme.

EXAMPLE 3

Physical Properties of the Enzyme

Figure 5:
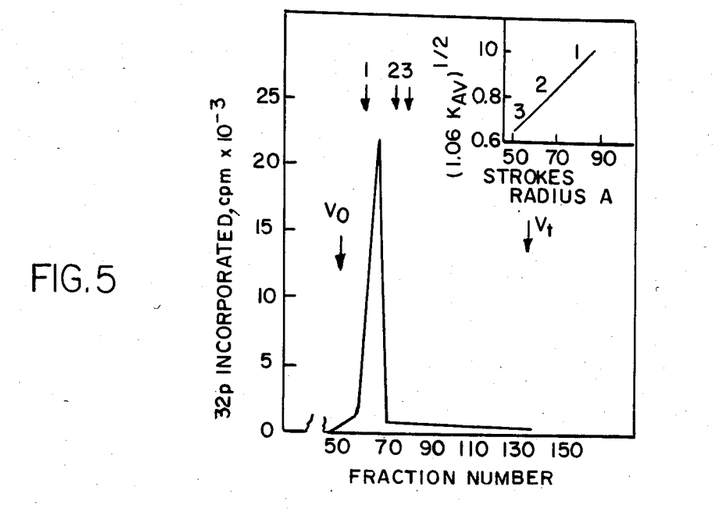
FIG. 5 describes the Stokes radius calculations for AUT-PK 500 and depicts Ultragel ACA-34 column chromatography of phosphorylated AUT-PK 500.
Figure 6:
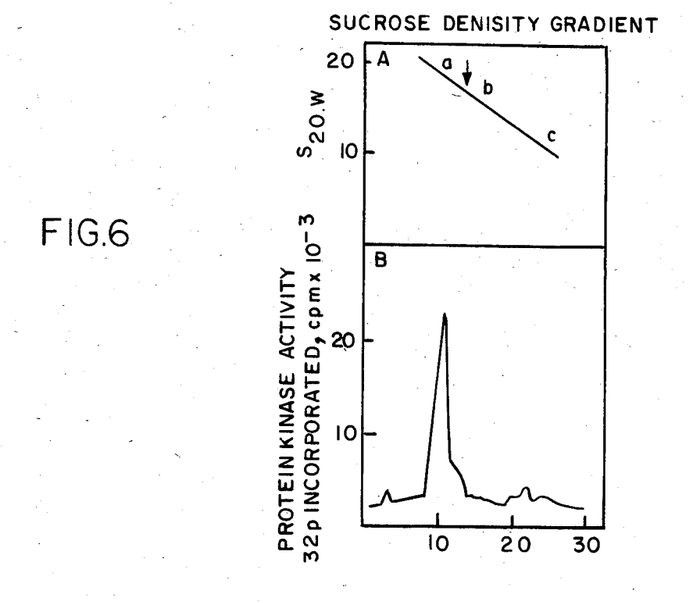
FIG. 6 describes the sucrose density gradient calculations for AUT-PK 500 and the endogenous protein kinase activity of isolated sucrose gradient fractions.

A Stokes radius of 66 angstroms was determined by gel filtration on ACA-34 (FIG. 5), and an $S_{W,20}$ of 18.20 was determined by sucrose density gradient centrifugation (FIG. 6). The molecular weight calculated from these parameters (Siegel et al., supra) was 490,000. Sedimentation equilibrium studies using the photoelectric scanner of the ultracentrifuge at 230 nm revealed a molecular weight of 481,000 (±7%). Since the enzyme showed a molecular weight of about 250,000 by SDS-polyacrylamide gel electrophoresis, this indicated that AUT-PK 500 is composed of two subunits of approximately identical size. The calculated frictional coefficient was 1.28, indicating that the molecule is slightly asymmetric (Delpaoli-Roach, et al., supra).

Figure 7:
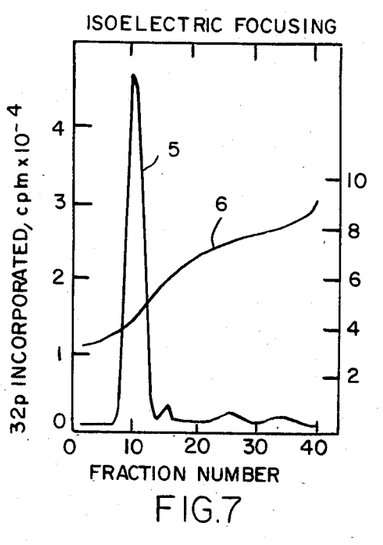
FIG. 7 depicts the isoelectric focusing gel results of AUT-PK, analyzed for protein kinase activity (5) and pH gradient (6)

To determine the pI value of the enzyme, AUT-PK 500 was subjected to isoelectric focusing (FIG. 7). As indicated by its pI of 4.6, the enzyme is acidic.

EXAMPLE 4

Identification of the Phosphorylated Amino Acid

The phosphate bond in self-phosphorylated AUT-PK 500 is acid-stable and alkali-labile, excluding the nature of the phosphorylated amino acids to the histidine or lysine. Tyrosine and serine are two other major amino acids that are phosphorylated in protein kinase reactions (Sharma et al., supra) and their phosphate bonds are not acid labile. In order to evaluate whether any of these amino acids is phosphorylated in the AUT-PK 500 autophosphorylation reaction, phosphorylated AUT-PK 500 containing $^{32}$P was acid hydrolyzed; authentic phosphoserine and phosphotyrosine were added to the hydrolyzed product and the resultant mixture was subjected to high voltage paper electrophoresis. Radioautographic analysis of the two ninhydrin stained spots revealed radioactivity only in phosphoserine (FIG. 8), indicating that the phosphorylated amino acid residue was serine.

In a separate experiment the phosphorylation of a threonine residue by the similar technique was evaluated, the results indicated that this amino acid was not phosphorylated in the autophosphorylation reaction.

EXAMPLE 5

Demonstration that AUT-PK 500 is a Novel Protein Kinase

Most of the known cyclic nucleotide-dependent or -independent protein kinases catalyze the phosphorylation of one or more of the commonly used exogenous substrates such as histone, casein, protamine, and phosvitin. None of these proteins affected the phosphorylation of AUT-PK 500 (Table II), suggesting that none of them was the substrate of the enzyme. In order to confirm this conclusion, AUT-PK 500 was incubated with [gamma-$^{32}$P] ATP and histone in the presence or absence of cyclic AMP, then subjected to SDS-polyacrylamide gel electrophoresis and analyzed by radioautography. There was no radioactivity corresponding to the histone band, indicating that histone is not the substrate of AUT-PK 500.

TABLE II

Substrate Specificity of AUT-PK 500 and and its Cyclic Nucleotide Independence
1 microgram of enzyme was assayed for autophosphorylation in the presence of different substrates, cyclic nucleotides and cyclic AMP-dependent protein kinase inhibitor, as indicated below.

| Additions | $^{32}$P Incorporated (cpm) |
|---|---|
| 1. Enzyme | 16,000 |
| 2. Enzyme + Casein (10 micrograms) | 10,000 |
| 3. Enzyme + Phosvitin (10 micrograms) | 15,000 |
| 4. Enzyme + Protamine (10 micrograms) | 12,000 |
| 5. Enzyme + Histone (10 micrograms) | 15,400 |
| 6. Enzyme + Cyclic AMP (1 microM) | 15,500 |
| 7. Enzyme + Histone (10 micrograms) + Cyclic AMP (1 microM) | 16,300 |
| 8. Enzyme + Cyclic AMP PK Inhibitor (10 micrograms) | 16,100 |
| 9. Enzyme + Cyclic GMP (1 microM) | 16,300 |
| 10. Enzyme + Cyclic GMP (1 microM) + Histone (10 micrograms) | 15,400 |

The two well characterized cyclic nucleotide-dependent protein kinases are cyclic AMP-dependent and cyclic GMP-dependent protein kinases (Krebs, supra, and Sharma, supra). Their activities are dependent on cyclic AMP and cyclic GMP, respectively. In addition, these two protein kinases can be differentiated from each other, since only cyclic AMP-dependent protein kinase activity is blocked by the heat-stable inhibitor (Ashby, C. D., and Walsh, D. A., *J. Biol. Chem.*, 247, 6637–6642 (1972)) and only cyclic GMP-dependent protein kinase phosphorylation of histones is stimulated by calmodulin or troponin (Ahrens et al., supra). The AUT-PK 500 activity was independent of cyclic AMP and cyclic GMP and not blocked by the heat-stable inhibitor (Table III). In addition, since AUT-PK 500 did not phosphorylate histone or casein, these results together demonstrate that AUT-PK 500 is not a cyclic nucleotide-dependent protein kinase.

As the names indicate, calcium- and calcium-calmodulin-dependent protein kinases are regulated by calcium and calcium-calmodulin. AUT-PK 500 activity was not affected by either calcium or calcium-calmodulin (Table III); there was a small (23.2%) inhibition by 1,2-di(2-aminoethoxy)ethane-N,N,N',N'-tetraacetic acid (EGTA), which could be explained by partial chelation of $Mg^{2+}$ used in the protein kinase buffer. These results indicate that AUT-PK 500 is both a calcium- and a calcium-calmodulin independent protein kinase.

TABLE III

Effect of Calcium, Calmodulin and EGTA on Autophosphorylatio of AUT-PK 500
1 microgram of enzyme was assayed for autophosphorylation of AUT-PK 500 in the presence of different effector molecules.

| Additions | $^{32}$P incorporated (cpm) |
|---|---|
| Enzyme | 18,500 |
| Enzyme + EGTA (0.8 mM) | 14,200 |
| Enzyme + $Ca^{2+}$ (0.4 mM) | 17,000 |
| Enzyme + Calmodulin (100 microgram/ml) | 17,400 |
| Enzyme + $Ca^{2+}$ + Calmodulin | 16,300 |

Reticulocytes contain several cyclic nucleotide-independent protein kinases such as casein kinases I and II (Hathaway et al., supra, and Tuazon et al., *Eur. J. Biochem.*, supra), the hemin-controlled repressor (Farrell et al., supra, Gross et al., supra, Ranu et al., supra, Traschsel et al., supra, and Tahara et al., *Proc. Natl. Acad. Sci. U.S.A.*, supra), the dsRNA-activated inhibitor (Farrell et al, supra, Levin et al., supra, and Lenz et al., supra), protease activated kinase I (Tahara et al., *J. Biol. Chem.*, supra) and protease activated kinase II (Tuazon et al., *J. Biol. Chem.*, supra). The substrates for these enzymes are casein and eIF-2beta for casein kinases I and II; eIF-2alpha for HCR; eIF-2beta and histones for dsRNA; casein for protease-activated kinase I; casein and eIF-2beta for protease-activated kinase II (Traugh, J. A., DelGrande, R. W., and Tuazon, P. T. in *Protein Phosphorylation*, Cold spring Harbor Conference on Cell Proliferation 8, 999–1012 (1981)). AUT-PK 500 did not phosphorylate any of these substrates, indicating that it is distinct from these protein kinase enzymes.

Figure 8:
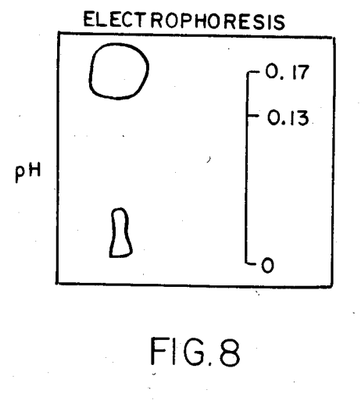
FIG. 8 depicts the characterization of endogenously phosphorylated amino acid residue (serine(s)) of AUT-PK 500, subjected to electrophoresis, stained with ninhydrin and autoradiographed.

AUT-PK B 500 is also distinct from tyrosine kinases (Ushiro et al, supra, Carpenter et al, supra, Cohen, S. et al., supra, Witte et al., supra, Eckhart et al., supra, and Beemon, supra), since it did not phosphorylate its tyrosine residue (FIG. 8). Another protein kinase, SPK 380, self-phosphorylates its histidine residue (Kuroda et al., *Arch. Biochem.,. Biophys.*, supra) and the partially purified enzyme catalyzes the phosphorylation of the serine residue residing in eIF-2alpha (Kuroda et al., *Arch. Biochem. Biophys.*, supra). Since AUT-PK 500 self-phosphorylated its serine residue and did not catalyze the phosphorylation of eIF-2alpha, this enzyme is not SPK 380.

EXAMPLE 6

Time Course of Self-Phosphorylation of AUT-PK 500

Figure 9:
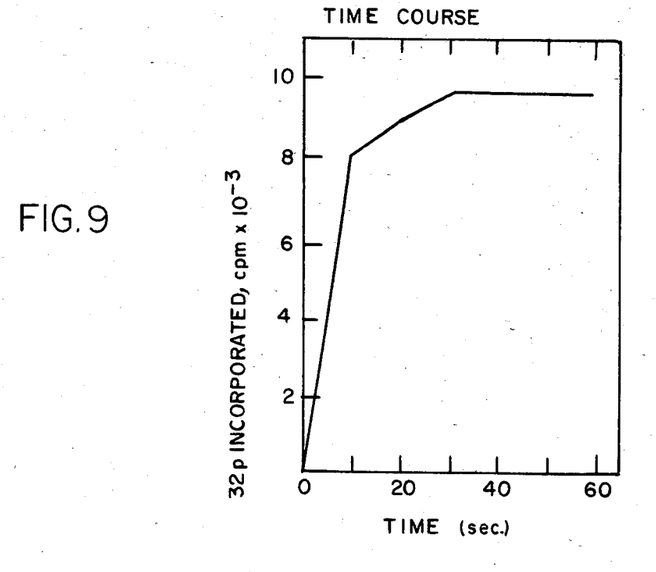
FIG. 9 describes the time course assay of autophosphorylation of AUT-PK 500.

To study the time course of AUT-PK 500 self-phosphorylation, the incorporation of [gamma-$^{32}$P] from [gamma-$^{32}$P] ATP into the 250,000-dalton subunit was measured (FIG. 9). The initial rate was rapid and linear through 10 sec., and almost completed in 30 sec. The stoichiometry of phosphate incorporation was 0.3 mol/mol of holoenzyme. This may not reflect true stoichiometry of phosphate in the holoenzyme, since the original enzyme could exist in a partially phosphorylated state.

The autophosphorylation of AUT-PK 500 was determined over a range of ATP concentrations. The reaction rate was hyperbolic and was dependent on ATP concentration in a saturable manner.

EXAMPLE 7

ATP Specificity of AUT-PK 500

When [gamma-$^{32}$P] GTP was used as phosphate donor, no incorporation of radioactivity was observed, indicating a specificity for ATP. Furthermore, GTP did not affect the ATP-dependent rate of self-phosphorylation.

EXAMPLE 8

Polyamine Effect on the Autophosphorylation of AUT-PK 500

No effect of the polyamines putrescine, spermine, and spermidine each at 1 mM concentration, or of polylysine and polyarginine in concentrations of up to 200 micrograms/ml, on the autophosphorylation of AUT-PK 500 was detected either by filter assay or by radioautographic analysis of the SDS-polyacrylamide gel resolved enzyme.

EXAMPLE 9

Effect of Divalent Cations

Figure 10:
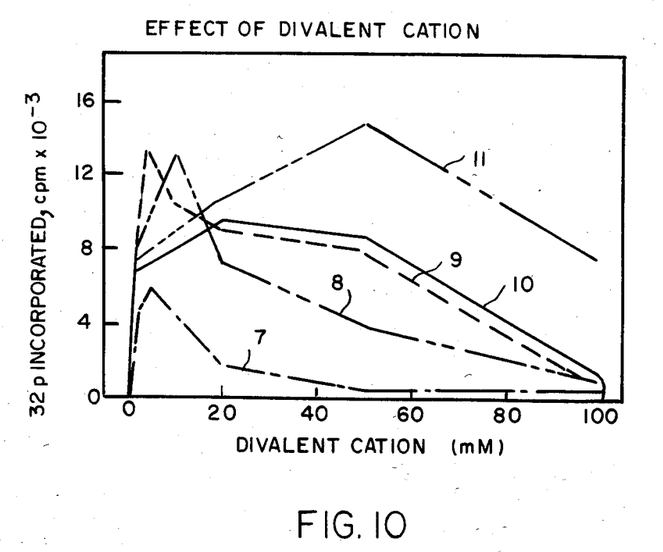
FIG. 10 describes the effect of various divalent cations on the autophosphorylation of AUT-PK 500.

Each of the divalent cations, $Mg^{2+}$, $Mn^{2+}$, $Sr^{2+}$ and $Co^{2+}$ at 2.5 mM concentration resulted in half-maximal stimulation of AUT-PK 500. However, peak activity of the enzyme was obtained with 5 mM $Mn^{2+}$ and $Co^{2+}$, 10 mM $Mg^{2+}$, 20 mM $Ca^{2+}$ and 50 mM $Sr^{2+}$. The maximal activation by $Co^{2+}$ was 40% and by $Ca^{2+}$, 60%, of that obtained by $Mn^{2+}$ or $Mg^{2+}$. The maximal activation by $Sr^{2+}$ was of the same order as that by $Mn^{2+}$ or $Mg^{2+}$ (FIG. 10).

Monovalent cations, such as sodium, potassium, and lithium, in concentrations of up to 100 mM, showed no significant effect on the AUT-PK 500 activity.

EXAMPLE 10

Other Properties of AUT-PK 500

The optimum pH for AUT-PK 500 activity was 7.5. N-ethylmaleimide and p-chloromercuriphenylsulfonic acid, which inhibit the activity of enzymes dependent on the structural requirement of sulfhydryl groups, did not influence AUT-PK 500 activity (see Table IV).

TABLE IV

SH Group Inhibitor Effect on Antophosphorylation of AUT-PK 500
1 microgram of enzyme was assayed in the presence of different -SH group inhibitors as indicated below. The enzyme activity was measured under standard conditions.

|  | $^{32}P$ Incorporated (cpm) |
| --- | --- |
| Enzyme | 18,500 |
| Enzyme + N—Ethylmaleimide (5 mM) | 18,000 |
| Enzyme + Iodoacetamide (5 mM) | 18,600 |
| Enzyme + p-chloromercuri-phenylsulfonic acid (5 mM) | 18,300 |

EXAMPLE 11

Immunoelectrophoretic Purity of AUT-PK 500

Figure 11:
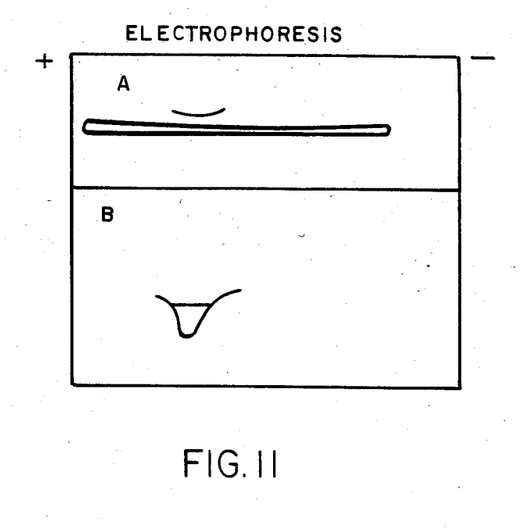
FIG. 11 depicts (A) the electrophoresis in agarose gel of AUT-PK 500 as analyzed by immunodiffusion precipitation with rabbit anti-AUT-PK 500 IgG and (B) the electrophoresis in agarose gel of AUT-PK 500 followed by crossed immune electrophoresis in gel containing rabbit anti-AUT-PK 500 IgG.

Immunoelectrophoresis and crossed immune electrophoresis analyses of the purified AUT-PK 500 with the use of the rabbit anti-AUT-PK 500 IgG both demonstrated single arcs of precipitation (FIG. 11). Control tests in which normal rat serum was substituted for AUT-PK 500 in reactions with the specific immune IgG and in which pre-immune rabbit IgG was substituted for the specific immune IgG in reactions with the enzyme were negative. These results were indicative of the homogeneity of the enzyme and demonstrated the specificity of the anti-AUT-PK 500 IgG. In other experiments, the enzyme was either phosphorylated with [gamma-$^{32}$P] ATP or isotopically labeled with $^{125}$I, immunoprecipitated with the specific anti-AUT-PK 500 IgG, and then resolved by SDS-polyacrylamide gel electrophoresis. Radioautographic analysis of the gels showed a single phosphorylated or iodinated protein which comigrated identically with the Coomassie Blue-stained band, thus providing additional evidence for purity of the enzyme.

EXAMPLE 12

Immunofluorescence Localization of AUT-PK 500

Figure 12A:
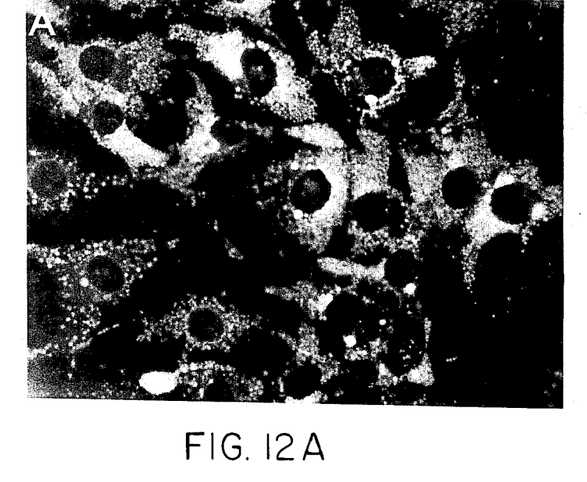
FIG. 12 depicts (A) the vesicular cytoplasmic and perinuclear distribution of AUT-PK 500 in the RADC$_4$ tumor cell line and (B) the homogeneous cytoplasmic distribution and perinuclear concentration of AUT-PK 500 in freshly isolated rat adrenocortical carcinoma 494.
Figure 12B:
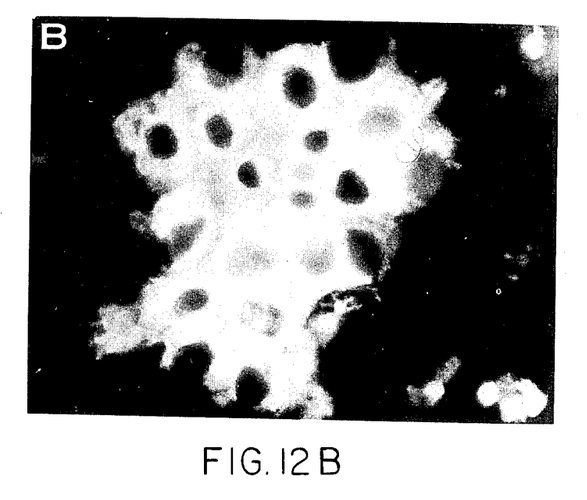

Indirect immunofluorescence observations with anti-AUT-PK 500 IgG revealed an intracytoplasmic localization of the enzyme in the fixed RADC$_4$ cell monolayers and in the freshly isolated tumor cells. The patterns of localization differed, however, with the enzyme concentrated in densely fluorescent vesicles of the cultured cells (FIG. 12A), while demonstrating a smooth, homogeneous cytoplasmic distribution in the freshly isolated cells (FIG. 12B). Cells from both sources presented an intensity of perinuclear enzyme fluorescence, but AUT-PK 500 was not apparent in the nuclei or nucleoli. Studies of viable RADC$_4$ cell membranes were negative indicating that if expressed on the membrane, the AUT-PK 500 was in concentrations too low for immunofluorescence detection. Control assays with pre-immune rabbit serum IgG and direct tests with fluorescein-conjugated goat anti-rabbit IgG were negative, supporting the specificity of the immunofluorescence observations.

EXAMPLE 13

Immunological Evidence for the Autophosphorylation Characteristic of AUT-PK 500

Figure 13:
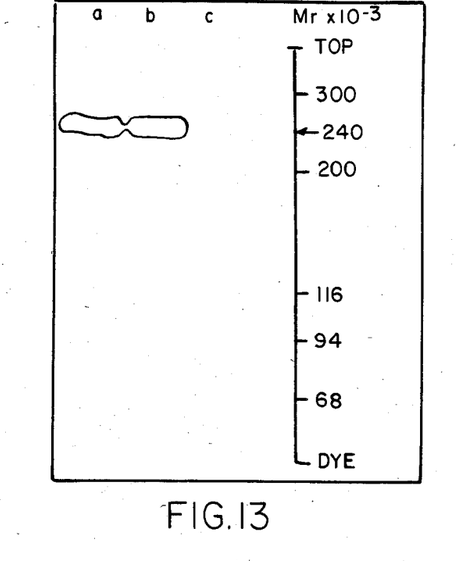
FIG. 13 depicts the one dimensional SDS-polyacrylamide gel electrophoresis and autoradiography of autophosphorylation attempts of (a) AUT-PK 500; (b) AUT-PK 500 and pre-immune serum IgG; and (c) AUT-PK 500 and anti-AUT-PK 500 IgG.

When AUT-PK 500 was incubated in the presence of anti-AUT-PK 500 IgG and [gamma-$^{32}$P] ATP, analysis by one-dimensional SDS-polyacrylamide gel electrophoresis followed by radioautography demonstrated that the antibody blocked the self-phosphorylation reaction of the enzyme (FIG. 13).

EXAMPLE 14

Evidence that Membrane-Bound 31,000 Molecular Weight Protein is a Substrate of AUT-PK 500

Figure 14:
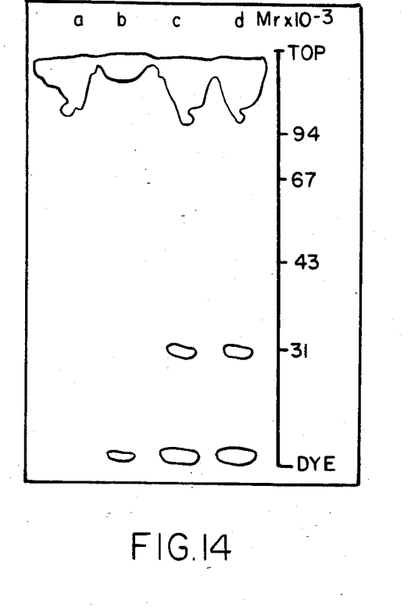
FIG. 14 depicts the one dimensional SDS-polyacrylamide gel electrophoresis and autoradiography results for autophosphorylation by AUT-PK 500 of membrane-bound ribosomal proteins; (a) AUT-PK 500; (b) membrane-bound ribosomal proteins; (c) AUT-PK 500 and membrane-bound ribosomal proteins; (d) AUT-PK 500, membrane-bound ribosomal proteins and cyclic AMP-dependent protein kinase inhibitor.
Figure 15:
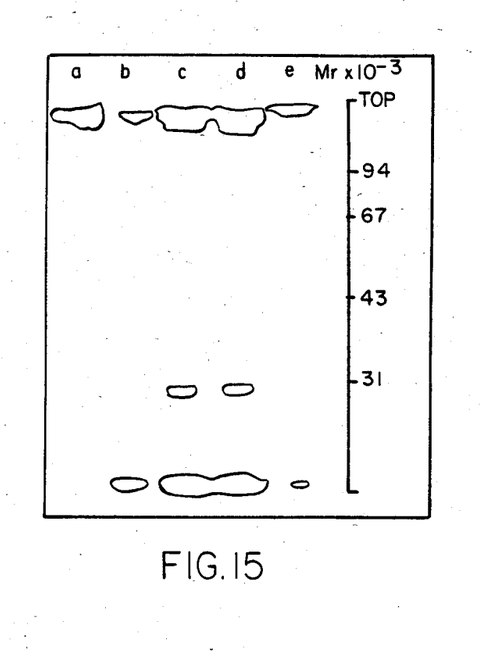
FIG. 15 depicts the one dimensional SDS-polyacrylamide gel electrophoresis and autoradiography results for blockage of autophosphorylation by AUT-PK 500 of the 31,000 molecular weight membrane-bound ribosomal protein by rabbit anti-AUT-PK 500 IgG.

In the presence of [gamma-$^{32}$P] AUT-PK 500 phosphorylated a 31,000 molecular weight membrane-bound ribosomal protein. The reaction was insensitive to the cyclic AMP-dependent protein kinase inhibitor (FIG. 14). The specific anti-AUT-PK 500 IgG blocked the AUT-PK 500-dependent phosphorylation of the 31,000 molecular weight protein (FIG. 15).

What is claimed is:

1. The substantially purified enzyme, autophosphorylating protein kinase, AUT-PK 500, free from other tissue culture components, and having the physical characteristics:
   (a) molecular weight as determined by sucrose density sedimentation—490,000;
   (b) molecular weight as determined by ultracentrifuge—481,400 (±7%);
   (c) asymmetric molecular configuration;
   (d) frictional coefficient—1.28;
   (e) sedimentation coefficient—18.20;
   (f) Stokes radius—66 angstroms;
   (g) optimum activity pH—7.5;
   (h) pI—4.6;
   (i) phosphate bond—acid stable and alkali labile;
   (j) autophosphorylates serine residues but not threonine;
   (k) activity unaffected by polyarginine;
   (l) autophosphorylation activated by the divalent cations $Mg^{2+}$, $Mn^{2+}$, $Sr^{2+}$, $Co^{2+}$ or $Ca^{2+}$.

2. The enzyme of claim 1 having a specific activity of at least 1000 units/mg.

3. The enzyme of claim 1 having a specific activity of at least 1500 units/mg.

4. An antibody, having the antigen-binding characteristics of anti-AUT-PK 500.

5. The antibody of claim 4 which is, anti-AUT-PK 500 IgG.

6. A diagnostic immunoassay method for detecting the presence of mammalian neoplasia which comprises contacting a substance to be tested for neoplasia with an antibody which specifically binds to one or more antigenic determinants of the enzyme AUT-PK 500 and measuring materials bound by said antibody.

7. The method of claim 6 wherein the antibody is anti-AUT-PK 500 IgG.

8. The method of claim 6 wherein the substance to be tested is analyte prepared from cells.

9. The method of claim 6 wherein the substance to be tested is fresh tissue.

10. The method of claim 6 wherein the substance to be tested is tissue prepared from a cryostat section.

11. The method of claim 6 wherein the substance to be tested is formalin fixed paraffin embedded tissue.

12. The method of claim 6 wherein AUT-PK 500 is coupled to a chemical label selected from the group consisting of enzymes, radionucleotides or fluorescent species.

13. The method of claim 12 wherein said chemical label is a radionucleotide.

14. The method of claim 13 wherein said radionucleotide is Iodine-125.

15. A diagnostic immunoassay kit comprising in packaged combination, a first container containing a quantity of the enzyme AUT-PK 500 sufficient for conducting an immunoassay and a second container containing a sufficient quantity of an antibody which specifically binds to one or more antigenic determinants of AUT-PK 500, said antibody having the antigen-binding characteristics of anti-AUT-PK 500.

16. The diagnostic kit of claim 15 wherein said antibody is anti-AUT-PK 500.

17. The diagnostic kit of claim 15 wherein said enzyme AUT-PK 500 is associated with a chemical label selected from the group consisting of enzymes, radionucleotides or fluorescent species.

18. The diagnostic kit of claim 17 wherein said chemical label is a radionucleotide.

19. The diagnostic kit of claim 18 wherein said radionucleotide is Iodine-125.

20. The diagnostic kit of claim 16 wherein said antibody is associated with a chemical label selected from enzymes, radionucleotides or fluorescent species.

21. The diagnostic kit of claim 20 wherein said chemical label is a radionucleotide.

22. The diagnostic kit of claim 21 wherein said radionucleotide is Iodine-125.

* * * * *